United States Patent
Bharti et al.

(10) Patent No.: US 8,024,974 B2
(45) Date of Patent: Sep. 27, 2011

(54) CANTILEVERED BIOACOUSTIC SENSOR AND METHOD USING SAME

(75) Inventors: Vivek Bharti, Cottage Grove, MN (US); Hatim M. Carim, West St. Paul, MN (US); Fred L. DeRoos, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 11/286,883

(22) Filed: Nov. 23, 2005

(65) Prior Publication Data

US 2007/0113649 A1    May 24, 2007

(51) Int. Cl.
  *G01N 29/00*    (2006.01)
(52) U.S. Cl. .............................. 73/591; 381/67
(58) Field of Classification Search ............... 381/67
  See application file for complete search history.

(56) References Cited

U.S. PATENT DOCUMENTS

| | | | |
|---|---|---|---|
| 3,182,129 A | | 11/1962 | Clark et al. |
| 3,682,161 A | | 8/1972 | Alibert |
| 4,008,408 A | | 2/1977 | Kodama |
| 4,012,604 A | | 3/1977 | Speidel |
| 4,127,749 A | | 11/1978 | Atoji et al. |
| 4,295,471 A | | 10/1981 | Kaspari |
| 4,672,976 A | * | 6/1987 | Kroll ............................ 600/528 |
| 4,708,019 A | * | 11/1987 | Rubner et al. .................. 73/760 |
| 4,855,544 A | * | 8/1989 | Glenn .................... 200/61.45 R |
| 4,884,809 A | | 12/1989 | Rowan |
| 5,036,857 A | * | 8/1991 | Semmlow et al. ............. 600/528 |
| 5,365,937 A | | 11/1994 | Reeves et al. |
| 5,383,473 A | * | 1/1995 | Moberg ......................... 600/595 |
| 5,425,750 A | * | 6/1995 | Moberg ........................ 607/19 |
| 5,496,352 A | | 3/1996 | Renger |
| 5,497,426 A | | 3/1996 | Jay |
| 5,539,831 A | | 7/1996 | Harley |
| 5,566,671 A | | 10/1996 | Lyons |
| 5,610,987 A | | 3/1997 | Harley |
| 5,807,268 A | | 9/1998 | Reeves et al. |
| 5,834,650 A | * | 11/1998 | Kim ............................... 73/651 |
| 5,853,005 A | | 12/1998 | Scanlon |
| 5,913,829 A | | 6/1999 | Reeves et al. |
| 6,002,963 A | | 12/1999 | Mouchawar et al. |
| 6,028,942 A | | 2/2000 | Greenberger |

(Continued)

FOREIGN PATENT DOCUMENTS

CN          2162654 Y        4/1994

(Continued)

OTHER PUBLICATIONS

U.S. Appl. No. 11/287,179, filed Nov. 23, 2005, Carim et al.

(Continued)

*Primary Examiner* — Robert R Raevis
(74) *Attorney, Agent, or Firm* — Kevin W. Weber (57) ABSTRACT

A sensor for sensing bioacoustic energy includes a housing comprising an interfacing portion configured to establish coupling with a body part during use of the sensor. An anchoring arrangement is defined on the housing. A transducer member has an anchoring end and at least one free end. The anchoring end of the transducer is coupled to the housing such that the transducer member is arranged to be preferentially sensitive to bioacoustic energy transferred to the transducer via the interfacing portion relative to other portions of the housing.

20 Claims, 7 Drawing Sheets

U.S. PATENT DOCUMENTS

| | | | |
|---|---|---|---|
| 6,261,237 B1* | 7/2001 | Swanson et al. | 600/527 |
| 6,324,289 B2* | 11/2001 | Orten | 381/67 |
| 6,347,147 B1 | 2/2002 | Downs, Jr. et al. | |
| 6,478,744 B2 | 11/2002 | Mohler | |
| 6,486,588 B2 | 11/2002 | Doron et al. | |
| 6,661,161 B1 | 12/2003 | Lanzo et al. | |
| 6,806,622 B1 | 10/2004 | Schmidt et al. | |
| 6,852,084 B1* | 2/2005 | Boesen | 600/528 |
| 6,954,971 B1* | 10/2005 | Bryant et al. | 29/25.35 |
| 6,988,993 B2 | 1/2006 | Sullivan et al. | |
| 7,155,281 B1* | 12/2006 | Fayram | 607/19 |
| 7,756,571 B1* | 7/2010 | Farazi | 600/517 |
| 2003/0214200 A1* | 11/2003 | Thompson et al. | 310/329 |
| 2004/0032957 A1 | 2/2004 | Mansy et al. | |
| 2004/0116969 A1* | 6/2004 | Owen et al. | 607/6 |
| 2004/0167417 A1* | 8/2004 | Schulhauser et al. | 600/513 |
| 2005/0014999 A1 | 1/2005 | Rahe-Meyer | |
| 2005/0043643 A1 | 2/2005 | Priemer | |
| 2005/0200242 A1 | 9/2005 | Degertekin | |
| 2005/0201576 A1 | 9/2005 | Barker et al. | |
| 2005/0232434 A1 | 10/2005 | Andersen | |
| 2007/0113654 A1 | 5/2007 | Carim et al. | |

FOREIGN PATENT DOCUMENTS

| | | |
|---|---|---|
| CN | 1159573 | 9/1997 |
| DE | 932268 | 8/1955 |
| DE | 2453926 | 11/1974 |
| DE | 2453926 | 5/1976 |
| DE | 2703781 | 1/1977 |
| DE | 2703781 | 8/1978 |
| EP | 0801927 | 10/1997 |
| EP | 0716628 | 2/1998 |
| EP | 0659058 | 1/1999 |
| GB | 2051584 | 7/1980 |
| JP | 317638 | 11/1992 |
| JP | 04335797 | 11/1992 |
| JP | 2004077346 * | 1/2004 |
| WO | 95/34917 | 12/1995 |
| WO | WO 96/027407 | 9/1996 |
| WO | 99/53277 | 10/1999 |
| WO | 00/10462 | 3/2000 |
| WO | 01/78059 | 10/2001 |
| WO | 01/097675 | 12/2001 |
| WO | 03/011132 | 2/2003 |
| WO | 2004/002191 | 12/2003 |
| WO | 2004/105612 | 12/2004 |

OTHER PUBLICATIONS

"MiniSense 100 Vibration Sensor" Measurement Specialties, Inc. www.meas-spec.com (Apr. 2006) p. 22.

Office Action dated Apr. 8, 2008 in U.S. Appl. No. 11/287,179.

Bizet, K., et al., "Biosensors based on piezoelectric transducers," Analusis, Wiley-VCH, 1999, 27, N° 7, pp. 609-616.

* cited by examiner

CANTILEVERED BIOACOUSTIC SENSOR AND METHOD USING SAME

FIELD OF THE INVENTION

The present invention relates to medical sensing devices and, more particularly, to sensors and devices incorporating such sensors whose input is variations of bioacoustic energy and output is a conversion to another form of energy.

BACKGROUND

A variety of devices have been developed to detect sounds produced by the body, such as heart sounds. Known devices range from primarily mechanical devices, such as the stethoscope, to various electronic devices, such as microphones and transducers. The stethoscope, for example, is a fundamental tool used in the diagnosis of diseases and conditions of the cardiovascular system. It serves as the most commonly employed technique for diagnosis of such diseases and conditions in primary health care and in circumstances where sophisticated medical equipment is not available, such as remote areas.

Although many electronic stethoscopes are available on the market, they have yet to gain universal acceptance by the physicians and other medical practitioners. Possible reasons for non-acceptance of electronic stethoscopes include the production of noise or artifacts that disturb the clinician during patient evaluation, as well as limitations associated with amplification and reproduction of certain biological sounds of interest. For example, a biological sound may be present but masked by noise, or wholly absent, and many conventional electronic stethoscopes are not capable of distinguishing between these two cases.

Noise that impacts stethoscope performance may be defined as any signal other than that of interest. Various types of noise include external or ambient noise, noise related to auscultation, noise generated by the electronic circuits of the stethoscope, and noise of biological nature produced by the patient's body, for example.

There is a need for a bioacoustic sensor with improved sensitivity and robustness. There is a further need for such a sensor that may be incorporated in various types of medical sensing devices, such as stethoscopes, that provides for an improved signal-to-noise ratio relative to conventional implementations. The present invention fulfills these and other needs.

SUMMARY OF THE INVENTION

The present invention is directed to sensors for sensing bioacoustic energy and methods using same. According to an embodiment of the present invention, a sensor for sensing bioacoustic energy includes a housing comprising an interfacing portion. The interfacing portion of the housing is configured to establish coupling with a body part during use of the sensor. A transducer member comprises at least one free end and an anchoring arrangement. The transducer member is fixedly coupled to the housing at a single anchoring location via the anchoring arrangement such that the transducer member is arranged to be preferentially sensitive to bioacoustic energy transferred to the transducer via the interfacing portion of the housing relative to other portions of the housing. At least one conductor is coupled to the transducer member.

The anchoring arrangement may include a compliant coupling arrangement configured to compliantly couple the transducer member to the housing. The anchoring arrangement may include a rigid coupling arrangement configured to rigidly couple the transducer member to the housing. The anchoring arrangement, for example, may include a pedestal having a first end and a second end. The first end of the pedestal may be coupled to the interfacing portion of the housing and the second end of the pedestal may be coupled to the transducer member. The anchoring arrangement may define a unitary structure of the housing.

The housing of the sensor may be configured for hand-held coupling to a body part during use. The sensor may include a fixing arrangement coupled to the housing and configured to establish affixation between the housing and the body part during use. For example, the sensor may include an adhesion arrangement coupled to the housing and configured to establish adhesive coupling between the housing and the body part during use.

The transducer member may include only one free end or may include two or more free ends. The conductor(s) coupled to the transducer member may include at least one electrical conductor. In another configuration, the conductor(s) coupled to the transducer member may include at least one optical conductor. The optical conductor may be coupled to converter circuitry. The converter circuitry may be situated remote from the sensor and configured to convert a received optical signal to an output electrical signal. The converter circuitry may be coupled to one or more electrical-to-audio converters, such as a pair of earphones. The converter circuitry may be coupled to an interface configured to couple the converter circuitry to an electronic device situated remote from the sensor.

The housing of the sensor may include a base and a cover. The base may include the interfacing portion and the cover may be coupled to the base via a compliant joint arrangement. The cover may include acoustically absorptive material. The interfacing portion of the housing may range in stiffness from relatively pliable to substantially stiff or rigid. The interfacing portion of the housing may include or be formed from a polymeric material, a metal or alloy, a composite material, or a ceramic or crystalline material.

The transducer member may include first and second opposing major surfaces. The first and second major surfaces of the transducer member may be substantially parallel to the interfacing portion of the housing. The transducer member is preferably configured to sense sounds produced by matter of biological origin. The transducer member may be configured for auscultation.

The sensor may include an arrangement configured to modify a frequency response of the transducer member. For example, a mass element may be disposed proximate to the free end of the transducer member. In one implementation, the mass element may comprise magnetizable material. A magnet arrangement may be configured to magnetically interact with the magnetizable material of the mass element. The magnet arrangement may be configured to facilitate adjustment of the interaction between the magnet and the magnetizable material of the mass element.

The transducer member is preferably configured to modulate or generate an electrical signal in response to deformation of the transducer member. The transducer member may be planar or non-planar, such as in the case of a curved or corrugated configuration. The transducer member may comprise piezoelectric material, such as a piezoelectric film, or a piezoresistive material or element. The transducer member may comprise one or more strain gauges or one or more capacitive elements.

According to other embodiments, a sensor unit may include a multiplicity of transducer members of a type described herein. Each of the transducer members may be configured to have a frequency response differing from that of at least one other transducer member of the sensor. For example, each of the transducer members has a stiffness, weight, shape, and thickness, and at least one of the stiffness, weight, shape, and thickness of each of the transducer member may differ from that of at least one other transducer member of the sensor. In one configuration, each of the transducer members is supported from the housing by a common anchoring arrangement. In another configuration, each of the transducer members is supported from the housing by separate anchoring arrangements.

Gain control circuitry may be provided so that a gain response of each transducer member may be selectably adjustable. Noise cancellation circuitry may be provided, which may include an auxiliary transducer member disposed within the housing other than at the interfacing portion of the housing. Noise cancellation circuitry may be coupled to the transducer member and the auxiliary transducer.

A stethoscope may be implemented to include a sensor of a type described herein. The sensor of the may include a single transducer member or a multiplicity of transducer members of a type described herein. A helmet may be implemented to include one or more sensors of a type described herein, and may include noise cancellation circuitry.

A sensor may be implemented to include communications circuitry configured to facilitate wired or wireless communication between the sensor and a device external of the housing. A sensor may include signal processing circuitry, such as a digital signal processor, coupled to the transducer member. The signal processing circuitry may be configured to filter and/or perform analyses on a sense signal produced by the transducer member.

In accordance with another embodiment, a sensor for sensing bioacoustic energy includes a housing comprising an interfacing portion configured to establish coupling with a body part during use of the sensor. The sensor further includes a transducer member comprising an anchoring arrangement. The transducer member is fixedly coupled to the housing via the anchoring arrangement such that the transducer member is arranged to be preferentially sensitive to bioacoustic energy transferred to the transducer via the interfacing portion of the housing relative to other portions of the housing. One or more conductors are coupled to the transducer member. The anchoring arrangement may be configured to fixedly couple the transducer member to the housing at two or more spaced-apart anchoring locations of the transducer member.

In accordance with a further embodiment, a method of sensing bioacoustic energy involves establishing coupling between an interfacing portion of a sensor housing and a body part from which bioacoustic energy emanates. The method further involves exciting a transducer, disposed in the sensor housing and operable in a cantilever mode, in response to the bioacoustic energy. The method also involves modulating or generating a signal by the transducer in response to excitation of the transducer.

Establishing coupling may involve establishing hand-held coupling between the interfacing portion of the sensor housing and the body part. Coupling between the interfacing portion and the body part may be established via adhesion or a restraining arrangement fixable to the body.

The signal modulated or generated by the transducer may be an electrical signal, and the method may further involve converting the electrical signal to an optical signal and transmitting the optical signal remotely of the sensor housing. A frequency response of the transducer member may be modified. Noise cancellation may be performed using the transducer member and at least one auxiliary transducer member.

Communication may be established between a device disposed within the sensor housing and a device external of the sensor housing. Various forms of analog and/or digital signal processing and/or analyses may be performed on the signal modulated or generated by the transducer.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF VARIOUS EMBODIMENTS

In the following description of the illustrated embodiments, reference is made to the accompanying drawings that form a part hereof, and in which is shown by way of illustration, various embodiments in which the invention may be practiced. It is to be understood that the embodiments may be utilized and structural changes may be made without departing from the scope of the present invention.

The present invention relates to sensors that are configured to be sensitive to sounds produced by matter of biological origin. Sensors and devices incorporating such sensors include those configured for auscultation, and may be configured to be sensitive to sounds produced by the heart, lungs, vocal cords, or other organs or tissues of the body, for example. By way of example, a sensor of the present invention may be incorporated in an electronic stethoscope, a helmet, or other externally worn or coupled apparatus or instrument that senses sounds produced by the body. A sensor of the present invention may also be configured for temporary or permanent fixation within the body, such as a heart or lung sound monitor implanted within the body, for example.

Sensors of the present invention may be implemented to be preferentially sensitive to a range of frequencies associated with human hearing. It is understood, however, that frequencies associated with body sounds below and/or above the auditory range of frequencies may also be sensed by sensors of the present invention. For example, sensors of the present invention may be implemented to sense body sounds that have frequencies ranging between just above DC and about 25 kHz. Sensors of the present invention may produce an audible output that falls within the auditory frequency range, or may produce an electrical or optical sensor that includes content above and/or below the auditory frequency range.

Bioacoustic sensors of the present invention preferably incorporate a transducer that is configured to modulate or generate an electrical signal in response to deformation of the transducer. Suitable transducers are those that incorporate piezoelectric material (organic and/or inorganic piezoelectric material), piezoresistive material, strain gauges, capacitive or inductive elements, a linear variable differential transformer, and other materials or elements that modulate or generate an electrical signal in response to deformation. The transducer may be planar or non-planar, such as in the case of a curved or corrugated configuration. Suitable piezo materials may include polymer films, polymer foams, ceramic, composite materials or combinations thereof. Additionally, the present invention may incorporate arrays of transducers of the same or different transducer type and/or different transducer materials, all of which may be connected in series, individually, or in a multi-layered structure.

Piezoelectric film has been found to be a particularly useful transducing material for sensing bioacoustic energy, particularly when implemented in a transducer configured to operate in a cantilever mode. A suitable piezoelectric film for a bioacoustic sensor of the present invention is MINISENSE-100 available from Measurement Specialties, Inc. in Hampton, VA. A suitable transducer for use in a bioacoustic sensor of the present invention that incorporates piezoelectric film is disclosed in U.S. Patent Publication No. 2003/0214200, which is hereby incorporated herein by reference.

A cantilevered transducer as contemplated herein is one that includes a single anchoring end or location and at least one free end. In various embodiments, a cantilevered transducer of the present invention includes one anchoring end and one free end. In other embodiments, a cantilevered transducer of the present invention includes one anchoring end and more than one free end. Examples of such embodiments are discussed hereinbelow.

The inventors have found that a bioacoustic sensor incorporating a cantilevered transducer anchored to a housing of sufficient integrity provides for a significantly improved sensitivity over a non-cantilevered transducer arrangement. The sensitivity of such a cantilevered transducer may be further increased by the addition of a mass proximate to the free end of the transducer. In one experiment involving use of a piezoelectric film transducer, sensor sensitivity was improved by more than 20 times by having the transducer operate in a cantilever mode and by adding a mass to the free end of the transducer.

Figure 1:
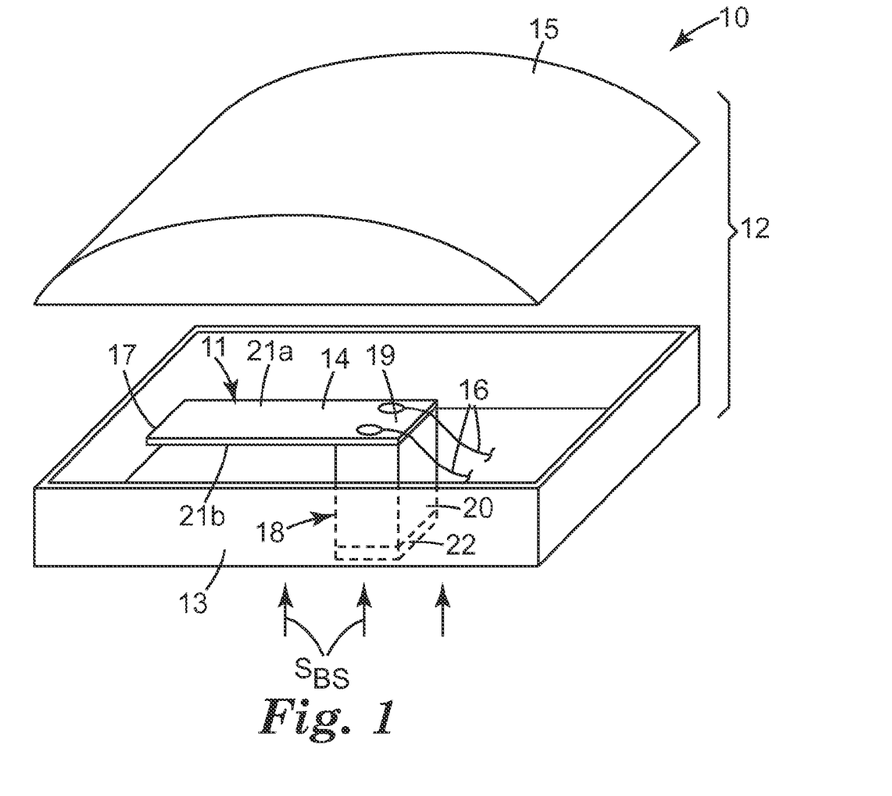
FIG. 1 is a diagram of a sensor that incorporates a transducer mounted to operate in a cantilever mode in accordance with an embodiment of the present invention.

Turning now to the figures, FIG. 1 illustrates a sensor that incorporates a transducer mounted to operate in a cantilever mode in accordance with an embodiment of the present invention. According to the embodiment of FIG. 1, a sensor 10 includes a housing 12 to which a transducer assembly 11 is mounted by way of an anchoring arrangement 18. The transducer assembly 11 includes a transducer 14 which is supported by, or otherwise mounted to, the anchoring arrangement 18. The transducer 14 includes one or more electrical contacts that allow for connection(s) to one or more conductors 16. The conductors 16 are typically electrical conductors or wires, but may alternatively be optical fibers coupled to electrical-to-optical converter circuitry, as in the case of an embodiment discussed hereinbelow.

In the embodiment shown in FIG. 1, the transducer 14 is mounted to the housing 12 in such a way as to operate in a cantilever mode. Many mounting configurations are contemplated that permit the transducer 14 to operate in a cantilever mode. The transducer 14 shown in FIG. 1 has a free end 17 and an anchoring end 19. The anchoring end 19 is coupled to an anchoring arrangement 18.

The anchoring arrangement 18 according to the embodiment illustrated in FIG. 1 includes a pedestal 20 which is affixed to the housing 12 at one end and coupled to the anchoring end 19 of transducer 14 at the other end. The pedestal 20 may vary in height from that shown in FIG. 1, but must provide sufficient clearance between the free end 17 of transducer 14 and housing surface or other potentially obstructive structure of the sensor 10 during operation. The pedestal 20 may be fixed to the housing 12 using a rigid or compliant fixation arrangement 22, such as an epoxy, a chemical bond, a weld or solder joint, a screw(s)/nut(s), rivet(s) or other mechanical coupling, or pressure sensitive adhesive, for example. A suitable fixation arrangement 22 may include No. 924 Scotch Adhesive Transfer Tape or No. DP100 Scotch Weld epoxy adhesive, both available from 3M, St, Paul, Minn.

It is believed that less compliant fixation arrangements should provide for better transmission of vibrations from the interfacing portion 13 of the housing to the pedestal 20 and transducer 14. The pedestal 20 or other form of anchoring arrangement 18 may define a unitary structure of the housing 12, such as a prominence protruding from the inside surface of housing 12 formed during molding of the housing 12.

The anchoring end 19 of transducer 14 may be pivotally or fixedly mounted to the pedestal 20. The transducer 14 is constructed so that a region defined between the free and anchoring ends 17, 19 is permitted to flex in response to forces acting on the transducer 14. Deformation of the transducer 14 during flexing facilitates modulation or generation of an electrical signal. Transducer 14 preferably incorporates piezoelectric material to transduce mechanical deformation of the transducer 14 into a measurable electrical parameter, although other materials and transducers are contemplated as previously discussed.

By way of non-limiting example, depending upon the configuration of transducer 14, the type of piezoresponsive material used, and the orientation and manner of deformation of the piezoresponsive material, a useful electrical response may be developed at electrodes located at various regions of the piezoresponsive material. Electrical connections can be made to conductive polymer, metallized foil, or conductive paint laminates or sandwiches containing the piezoresponsive material, for example. Measurable electrical parameters producible by such a piezoresponsive material include a voltage, current, or a change in electrical resistance.

It is known that certain semi-crystalline polymers, such as polarized fluoropolymer polyvinylidene fluoride (PVDF), have piezoelectric properties, which may include piezoelectric response. PVDF is used in various sensors to produce a voltage as a function of force or displacement. Polymer resin piezoelectric materials are particularly useful because the polymers can be embodied as sensing elements which are both flexible and elastic, and develop a sense signal representing resiliently biased deformation when subjected to force.

In one embodiment, transducer 14 includes a thin strip of a suitable piezoelectric polymer as a sensing element. The sensing element of transducer 14 is oriented so that the strip may be subject to deflection, which results in compression or tension of the sensing element in response to the applied force. Electrical contacts are made with the sensing element so that a voltage signal is produced in response to the force. Deformation of the sensing element of transducer 14 changes the relative positions of charges in the polymer chain or in the semi-crystalline lattice structure, thereby producing a voltage having an amplitude related (e.g., proportionally related) to the magnitude of the sensing element deformation.

The housing 12 shown in FIG. 1 includes an interfacing portion 13. Bioacoustic signals, SBS, produced from within the body, for example, are shown impinging on the interfacing portion 13. The interfacing portion 13 of the housing is configured to establish coupling with a body part during use of the sensor 10. For example, the interfacing portion 13 may be the surface of the housing 12 that comes into contact with a patient's chest or clothing covering the chest. The housing 12 also includes a non-interfacing portion 15, which may be a region of the housing 13 that faces the ambient environment during use of the sensor 10. The non-interfacing portion 15, which may be a separable cover, may incorporate acoustically absorptive material or other vibration attenuation material or arrangement.

The transducer assembly 11 is mounted within the housing 12 so that the transducer 14 is preferentially sensitive bioacoustic energy transmitted to the transducer 14 via the interfacing portion 13 relative to other portions of the housing 12, such as the non-interfacing portion 15. In the configuration shown in FIG. 1, for example, transducer 14 has two opposing major surfaces 21a, 21b. The transducer assembly 11 is mounted within the housing 12 so that the major surfaces 21a, 21b of the transducer 14 are substantially parallel to the interfacing portion 13 of the housing 14. Other orientations are possible depending on the particular transducer and housing features and characteristics. Preferred orientations between the transducer 14 and interfacing portion 13 of the housing 12 are those that provide for increased signal-to-noise ratios.

The interfacing portion 13 of the housing 12 is preferably formed from, or incorporates, material that facilitates transmission of vibrations from the interfacing portion 13 to the transducer 14, such vibrations resulting from bioacoustic energy emanating from the body and impinging on the housing 12. The interfacing portion 13 preferably has sufficient integrity to support the transducer 14. It has been found that a wide variety of materials having varying pliability may be used, ranging from relatively pliable to substantially stiff.

Suitable or workable materials for the interfacing portion 13 include polymeric materials, metals including alloys, composites, crystalline or ceramic materials. For example, suitable or workable materials include viscoelastic materials, foams (e.g., open cell polyurethane low-density foam), thermoplastic materials, thermosetting materials, paper materials (e.g., cardboard), and mineral materials (e.g., mica). Other examples include polycarbonate, styrene, ABS, polypropylene, aluminum, and other plastics and sheet metal alloys. It is understood that this listing of materials is for illustrative purposes only, and does not constitute an exhaustive identification of suitable or workable materials.

It is believed that use of relatively stiff material for the interfacing portion 13 increases the sensitivity of the transducer 14 to bioacoustic signals. It is believed that a wide range of materials and stiffness provides for enhanced transducer sensitivity.

Performance of sensor 10 may be enhanced by an arrangement configured to modify frequency response and/or sensitivity of the transducer 14. Such an arrangement may be a particular shape, stiffness, thickness and/or weight of the transducer 14. Altering one or more of these parameters can modify the frequency response and/or sensitivity of the transducer 14. In a sensor implementation that includes multiple transducers, for example, each transducer may provide for a different frequency response and/or sensitivity by having at least one of the stiffness, shape, thickness and/or weight differing from that of other transducers of the sensor.

Figure 2:
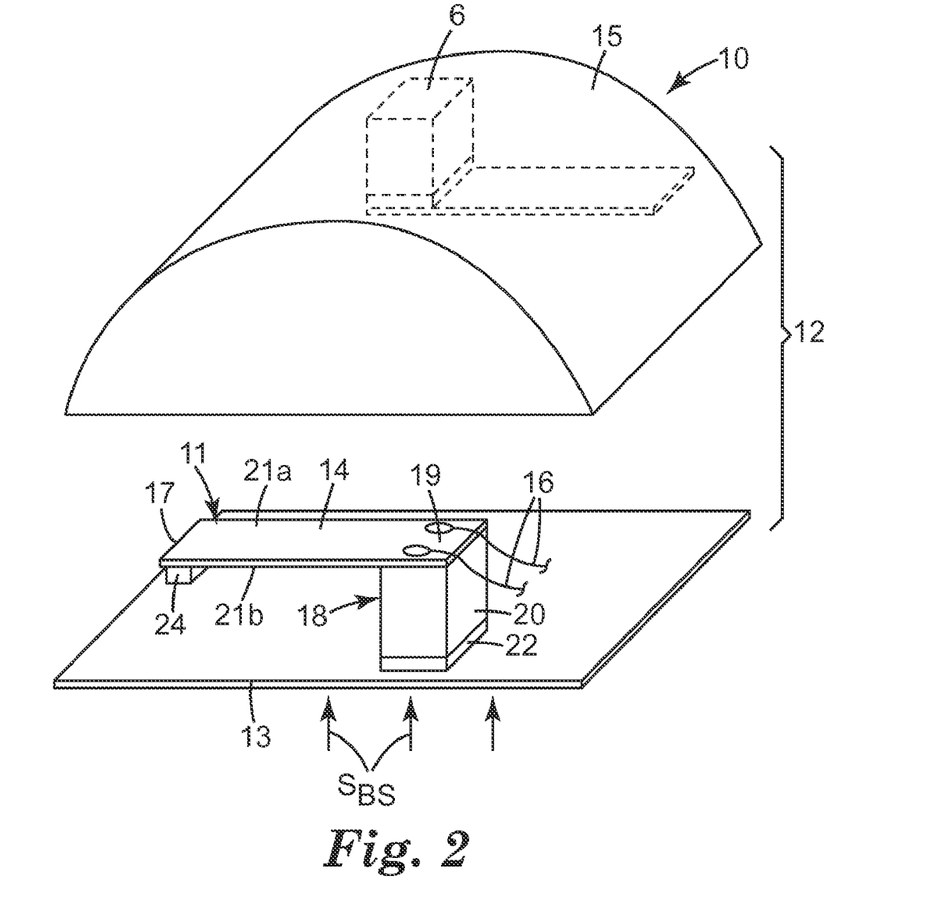
FIG. 2 is a diagram of a sensor that incorporates a weighted transducer mounted to operate in a cantilever mode, FIG. 2 further showing an optional auxiliary transducer that may be used to perform noise cancellation in accordance with an embodiment of the present invention.

FIG. 2 illustrates a sensor that incorporates a weighted transducer mounted to operate in a cantilever mode in accordance with an embodiment of the present invention. This embodiment is similar to that shown in FIG. 1, but with the addition of a mass 14 proximate to the free end 17 of the transducer 14. Addition of the mass 24 has been found to enhance the sensitivity of the transducer 14. Moreover, the presence of the mass 24 on the transducer 14 influences the frequency response and sensitivity of the transducer 14. It has been found that altering the weight and/or location of the mass alters the frequency response and/or sensitivity of the transducer 14. This phenomena may be exploited for purposes of adjusting the frequency response and/or sensitivity of a given transducer 14 to increase its sensitivity to a range of frequencies of particular interest.

For example, a first transducer of a sensor 10 may be properly weighted to be preferentially sensitive to heart sounds, while a second transducer of the sensor 10 may be properly weighted to be preferentially sensitive to lung sounds. By way of further example, a first transducer of a sensor 10 may be properly weighted to be preferentially sensitive to sounds associated with normal heart valve closure activity in the frequency range 10 to 200 Hz, while a second transducer of the sensor 10 may be properly weighted to be preferentially sensitive to sounds associated with abnormal heart valve closure activity (e.g., valve stenosis) in the 10 to 700 Hz range.

FIG. 2 further shows in phantom an optional auxiliary transducer 6 mounted within the housing 12. The auxiliary transducer 6 is preferably used to implement a noise cancellation methodology by the sensor 10. For example, the auxiliary transducer 6 may be mounted at a housing location that provides for preferential sensitivity to ambient noise. As shown in FIG. 2, auxiliary transducer 6 is mounted to the non-interfacing portion 15 (e.g., cover) of the housing 12. In this configuration, auxiliary transducer 6 is preferentially sensitive to vibrations resulting from ambient noise impinging on the non-interfacing portion 15 of the housing 12. The signal modulated or produced by the auxiliary transducer 6 may be used to cancel content of the signal modulated or produced by the transducer 14 that is attributable to ambient noise.

Various known methods of effecting noise cancellation using signals modulated or produced by auxiliary transducer 6 and transducer 14 may be used. The auxiliary transducer 6 may of the same or similar construction and configuration as transducer 14 or may be of a different construction and configuration.

Figure 3:
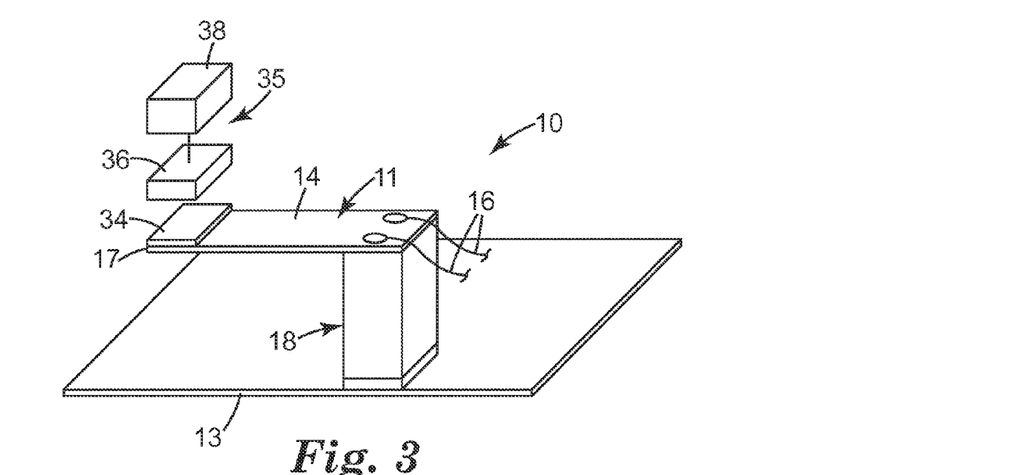
FIG. 3 is a diagram of a sensor that incorporates a weighted transducer mounted to operate in a cantilever mode and a magnetic control arrangement that magnetically interacts with the weighted transducer to modify the transducer's frequency response in accordance with an embodiment of the present invention.

FIG. 3 is a diagram of a sensor that incorporates a weighted transducer mounted to operate in a cantilever mode and a magnetic control arrangement that magnetically interacts with the weighted transducer to modify the transducer's frequency response and/or sensitivity in accordance with an embodiment of the present invention. According to this embodiment, a mass 34 of magnetic or magnetizable material, such as a ferromagnetic weight, is disposed proximate to the free end 17 of the transducer 14.

A frequency response adjustment mechanism 35 is shown to include a magnet 36 coupled to an actuator 38. The magnet 36 may be a permanent magnet or an electromagnet. The actuator 38 and magnet 36 cooperate to adjust the strength of a magnetic field defined between the magnet 36 and mass 34. For example, the position of the magnet 36 relative to the mass 34 may be changed to adjust the strength of a magnetic field defined between the magnet 36 and mass 34. The change in relative position between the magnet 36 and mass 34 may be continuously variable or may be variable in a step-wise fashion. In the case of an electromagnet, the supply current may be adjusted to change the strength of the magnetic field.

The position of the magnet 36 relative to the weight 34 affects the damping of the transducer 14, thus changing the frequency response of the transducer 14. For example, with the magnet 36 positioned close to the mass 34, the transducer 14 would be more sensitive to high frequency sounds. With the magnet 36 positioned away from the mass 34, the transducer 14 would be more sensitive to lower frequency sounds. The frequency response adjustment mechanism 35 may be actuated (mechanistically or automatically) to effectively adjust the frequency response of the transducer 14, allowing the clinician to preferentially detect body sounds (e.g., heart sounds) having different frequency characteristics. One or more frequency response adjustment mechanisms 35 may be used for a given sensor 10.

Figure 4:
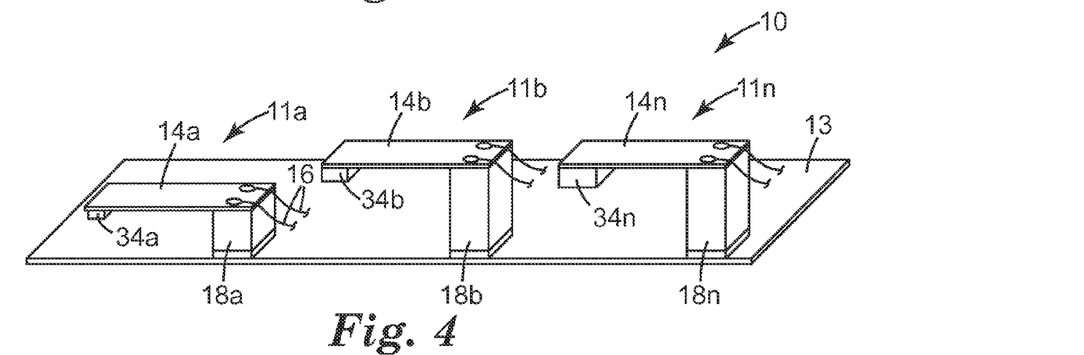
FIG. 4 is a diagram of a sensor that incorporates a multiplicity of transducer assemblies, the transducer of each transducer assembly configured to have a frequency response differing from other transducers of the sensor in accordance with an embodiment of the present invention.

FIG. 4 is a diagram of a sensor 10 that incorporates a multiplicity of transducer assemblies 11a-11n. The transducer 14a-14n of each transducer assembly 11a-11n is configured to have a frequency response differing from other transducers 14a-14n of the sensor 10. As was discussed previously, the frequency response of a transducer 14 is governed by several parameters, most notably the shape, stiffness, weight, and thickness of the effective transducing element of the transducer 14. Altering one or more of these parameters can modify the frequency response of the transducer 14. In the embodiment shown in FIG. 4, the mass 34a-34n of each transducer 14a-14n is of different weight, resulting in each transducer 14a-14n having a different frequency response. It is understood that one needs to be careful in preventing or filtering later any cross talk that may occur amongst the various transducer assemblies 11a-11n.

It is appreciated that other parameters can be varied among the transducer assemblies 11a-11n to achieve differing frequency responses and/or sensitivities, such as the location of the mass 34a-34n on the transducer 14a-14n. FIG. 4 shows other elements of the transducer assemblies 11a-11n that may be varied to provide for differing frequency response characteristics and/or sensitivity, such as the pedestal height of anchoring arrangements 18a-18n. The housing 12 and, more specifically, the interfacing portion 13, may include features that provide for a differing frequency response and/or sensitivity across an array of transducers 14a-14n. For example, the thickness, material, or other aspect of a region of the interfacing portion 13 that supports each transducer 14a-14n may be varied. Elements of varying shape and material may be inserted into the interfacing portion 13 so as to influence the frequency response and/or sensitivity of each transducer 14a-14n in a desired manner. As such, differences in the frequency response and/or sensitivity of multiple transducers 14a-14nmay be achieved at least in part by providing for differences in the housing construction or material in regions that support or influence each of the transducers 14a-14n.

Figure 5:
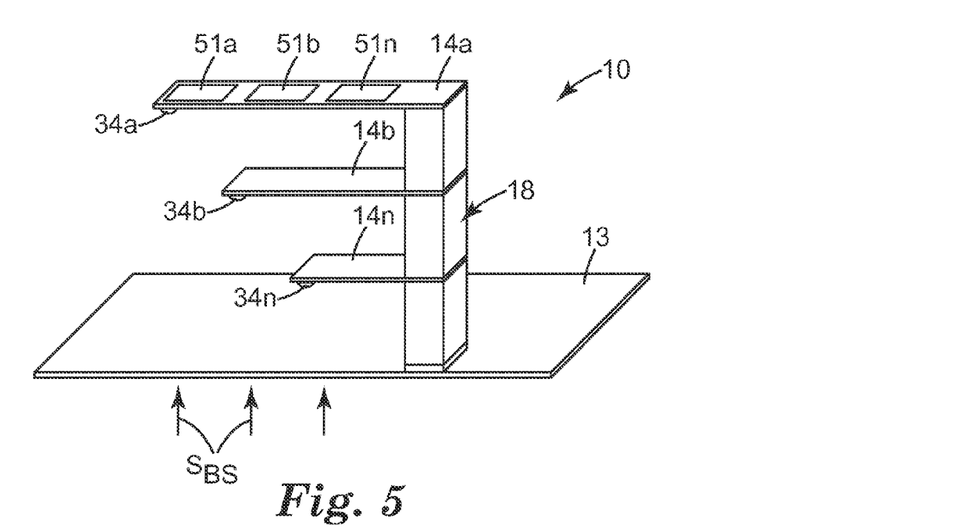
FIG. 5 is a diagram of a sensor that incorporates a multiplicity of transducers mounted to a common anchoring arrangement, the transducers configured to have a frequency response differing from other transducers of the sensor in accordance with an embodiment of the present invention.

FIG. 5 is a diagram of a sensor 10 that incorporates a multiplicity of transducers 14a-14n, which may be mounted to a common substrate. In this illustrative embodiment, each of the transducers 14a-14n has a length that differs from other transducers 14a-14n of the sensor 10. The weight of the masses 34a-34n of transducer 14a-14n in this embodiment is the same, it being understood that the masses 34a-34n may differ in weight and location. The transducers 14a-14n of varying length provide for sensitivity to body sounds of varying frequency.

FIG. 5 shows a number of discrete transducer elements 51a-51n mounted on a common substrate. Each of the discrete transducer elements 51a-51n is situated at a different location on transducer 14a. Hence, each discrete transducer element 51a-51n may be sensitive to excitations of differing frequency. The transducer elements 51a-51n may be of the same type and size or may differ in these or other characteristics. It is understood that individual transducers of a given multi-transducer assembly are preferably coupled to the sense/detection circuitry or processor of the sensor via individual channels, with appropriate buffering provided for each channel. Although such channels are typically defined by one or more conductors dedicated for each transducer, various time or frequency multiplexing techniques may be used to reduce to the complexity of the sensor's wiring scheme.

Clinicians readily appreciate that detecting relevant cardiac symptoms and forming a diagnosis based on sounds heard through a stethoscope, for example, is a skill that can take years to acquire and refine. The task of acoustically detecting abnormal cardiac activity is complicated by the fact that heart sounds are often separated from one another by very short periods of time, and that signals characterizing cardiac disorders are often less audible than normal heart sounds.

It has been reported that the ability of medical students to recognize heart murmurs correctly is poor. In one study, it was found that only 13.5±9.8% students were able to diagnose heart murmurs correctly, and that this does not improve with subsequent years of training by lectures, demonstration of heart sounds, and then clinical exposures. It has also been found, through psychoacoustic experimentation, that a sound needs to be repeated from 1200-4400 times for the brain to recognize differences. Using this information, studies have been performed to evaluate the effect of heart sound repetition on a doctor's ability to diagnose correctly. One such study was performed with 51 medical student doctors diagnosing four basic cardiac murmurs, where each murmur was repeated 500 times. Significant improvement (85±17.6%) of auscultatory proficiency was observed, demonstrating that repeating the heart sounds of interest some 500 times resulted in increased proficiency to correctly recognize basic cardiac murmurs.

It should be appreciated that there are more than 40 different known heart "murmur" sounds. This would make it challenging for doctors to listen to each heart sound 500 times and remember each of the 40 known heart sounds, as the brain has a tendency to loose the memory if the sound has not been heard for a long time.

The decline in the diagnostic skill of cardiac auscultation has contributed to a situation for both patients and physicians to rely on alternative diagnostic methods. It has been reported that nearly 80% of patients referred to cardiologists have normal hearts or only benign heart murmurs. Such false positives constitute a significant waste of time and expense for both patients and cardiologists.

A bioacoustic sensor of the present invention may be implemented to be sensitive to heart sounds of varying types and characteristics. For example, a sensor may incorporate several transducers, each of which is preferentially sensitive to a frequency or range of frequencies associated with one or a number of known heart sounds. For example, individual transducers may be "tuned" to detect particular heart murmurs. A switching or scanning technique may be employed by which each transducer of an array of transducers is selectively enabled for listening by the clinician or for output to a display/auditory device, such as by use of a wireless communication link.

In a more complex implementation, sound profiles of the 40 or more known heart sounds may be developed (e.g., signal morphological profiles or frequency spectrum profiles). A processor, such as a digital signal processor, may perform a comparison between detected heart sounds and heart sound profiles of a library of such profiles to determine presence or absence of particular heart sounds emanating from the patient. Various algorithms, such as correlation or pattern recognition algorithms, may be employed to perform the comparison.

The capability of adjusting the frequency response of the bioacoustic sensor 10 of the present invention advantageously allows a single sensor to have broadband sensitivity to a wide spectrum of body sounds, and the ability to target body sound frequencies of particular interest.

Figure 6:
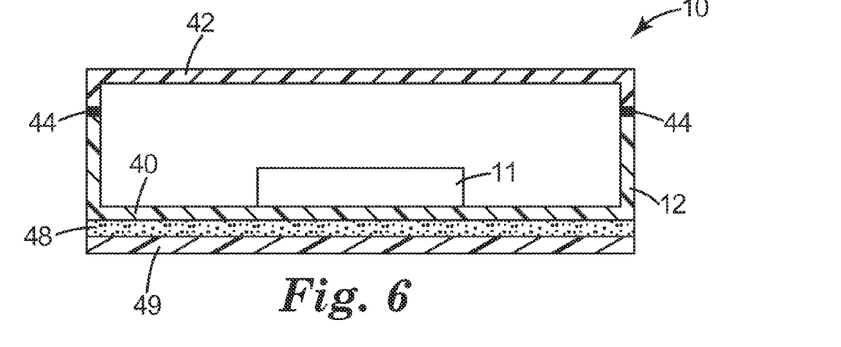
FIG. 6 is a diagram of a sensor that incorporates a transducer mounted in a housing, the housing including an adhesive layer that provides for intimate coupling between the housing and a body part during use in accordance with an embodiment of the present invention.

FIG. 6 is a diagram of a sensor 10 that incorporates a transducer assembly 11 disposed in a housing 12. The housing 12 includes an adhesive layer 48 that provides for intimate and secured coupling between the sensor housing 12 and a body part during use. A peel-away liner 49 may cover the adhesive layer 48 and be removed prior to use of the sensor 10. The adhesive layer 48 preferably provides for good acoustic coupling between the sensor 10 and the patient's body part (e.g., skin or outer clothing). Various known adhesives and peel-away liner arrangements may be employed. For example, adhesives similar to the pressure sensitive adhesive tapes used in the construction of electrocardiogram (ECG) electrodes to be adhered to skin may be used. One such tape is Micropore tape with adhesive, No. 9914, non-woven skin tape, available from 3M, St. Paul, Minn. A sensor configured according to FIG. 6 may be particularly useful in the context of a disposable sensing device, such as a disposable stethoscope.

The housing 12 shown in FIG. 6 is a two-part housing that includes a base 40 and a cover 42. The base 42 is preferably formed of a relatively stiff material, as the base 42 incorporates an interfacing portion as described hereinabove. The cover 42 may be formed from the same or different material as the base 40, and attached to the base 40 using a known coupling arrangement. A compliant interface 44 may be formed between the base 40 and cover 42. The compliant interface 44 is formed of a material that attenuates vibrations transmitted along or through the cover 42, typically produced from sources in the ambient environment. Also, and as previously discussed, cover 42 may be formed from acoustically absorptive material that aids in reducing transducer excitation due to ambient noise. Provision of vibration isolation/attenuation between the cover 42 and base 40 advantageously attenuates vibrations produced from such ambient sources (e.g., non-body produced sounds), thus increasing the sensitivity of the senor 10 to body produced sounds.

Figure 7:
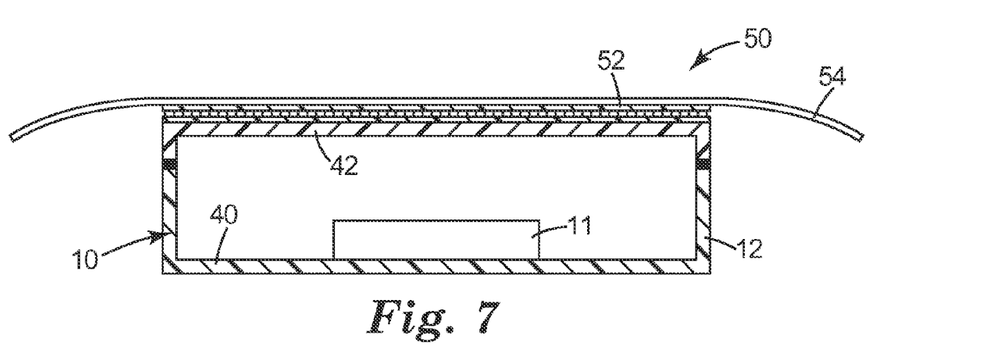
FIG. 7 is a diagram of a sensor that incorporates a transducer mounted in a housing, the housing including an elastic fixation arrangement that provides for intimate coupling between the housing and a body part during use in accordance with an embodiment of the present invention.

FIG. 7 is a diagram of a sensor 10 that incorporates a housing 12 having a fixation arrangement 50. The fixation arrangement 50 facilitates fixation of the sensor 10 to a patient's body part during use and easy removal from the patient after use. In the embodiment shown in FIG. 7, the fixation arrangement 50 includes one or more elastic bands 54 that are coupled to the housing 12 of the sensor 10. The elastic bands 54 are of sufficient length and elasticity to extend around the patient's body part of interest. The ends of the elastic bands 54 are provided with a suitable coupling arrangement that allows for secured engagement of sensor 10 to the patient during use. In an alternative configuration, the fixation arrangement 50 may include one or more strips of adhesive tape, which may be represented by adhesive (elastic or non-elastic) bands or strips 54 in FIG. 7.

In one implementation, and as shown in FIG. 7, the sensor 10 may be removable relative to the fixation arrangement 50. For example, a hook and loop interface 52 may be provided between the housing 12 and the elastic bands 54. Use of such a hook and loop interface 52 facilitates easy removal and replacement of the sensors 10 relative to the fixation arrangement 50. By way of example, several sensors 10 may be available to a clinician, each one being configured for sensing a particular body sound. Sensors 10 may be swapped during patient evaluation with relative ease, without having to adjust or remove the fixation arrangement 50.

Figure 8:
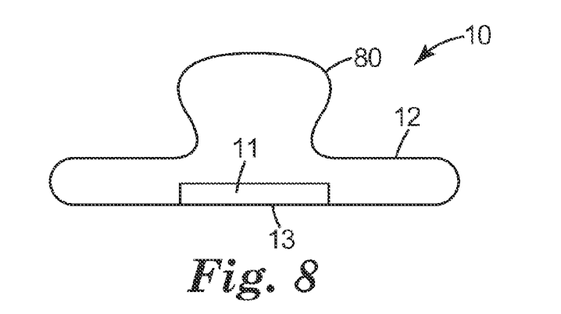
FIG. 8 is a diagram of a sensor that incorporates a transducer mounted in a housing, the housing shape configured for ease of hand manipulation to facilitate intimate coupling between the housing and a body part during use in accordance with an embodiment of the present invention.

FIG. 8 is a diagram of a sensor 10 that incorporates a housing 12 having a shape configured for ease of hand manipulation to facilitate manual coupling between the housing 12 and a body part during use in accordance with an embodiment of the present invention. The shape of the housing 12 may be ergonomically tailored to the specific use of the sensor. The housing 12 shown in FIG. 8 may facilitate ease of hand-held manipulation of the sensor 10. For example, a clinician may grasp the handle projection 80 of the housing 12 and apply the interfacing portion 13 of the housing to the patient's skin or outer clothing. The sensor 10 may be held in place by the clinician during the evaluation. It is understood that other housing shapes are contemplated.

Figure 9A:
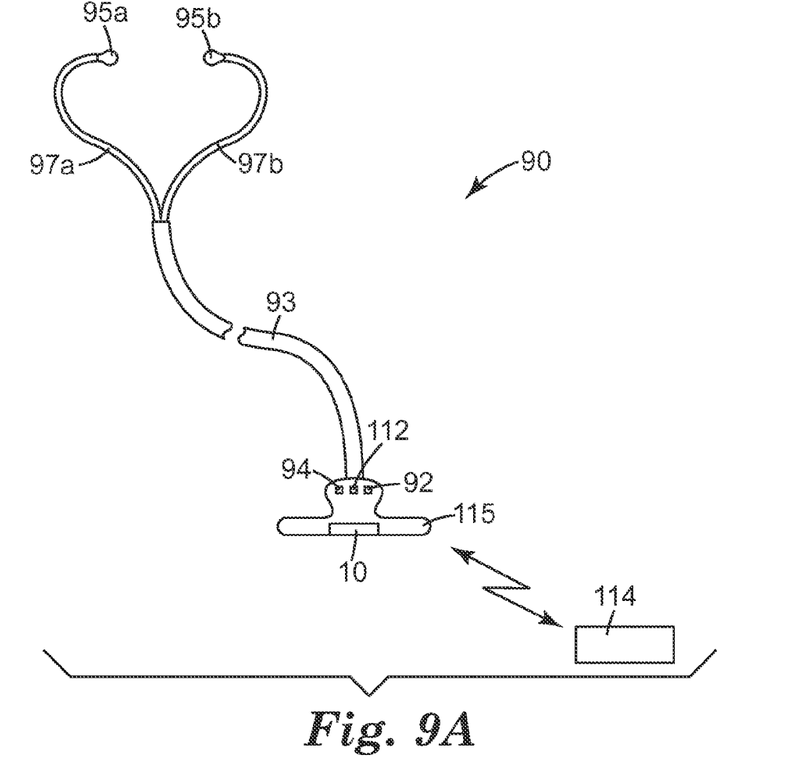
FIG. 9a shows a stethoscope that incorporates a sensor of the present invention.

FIG. 9a shows a stethoscope that incorporates a sensor of the present invention. The stethoscope 90 is an electronic stethoscope configured to include traditional components, such as a pair of ear pieces 95a, 95b, ear tubes 97a, 97b, and a main tube 93. The main tube 93 is coupled to a main housing 115, within which a sensor 10 of a type previously described is disposed. Other components that may be disposed in the main housing 115 include a power source 92, signal processing circuitry 94, and a communications device 112.

The signal processing circuitry 94 may perform more sophisticated analysis of bioacoustic signals received from the sensor 10, such as body sound profile matching as discussed above. The signal processing circuitry 94 may perform various forms of statistical analysis on signals produced by the sensor. In such configurations, the signal processing circuitry 94 may include a digital signal processor. Alternatively, or in addition, an external system 114 may perform all or some of such signal processing and analyses. The external system 114 may include a display, sound system, printer, network interface, and communications interface configured to establish uni- or bi-directional communication with the communications device 112 disposed in the main housing 115 of the stethoscope 90.

Communications device 112 may be implemented to establish a conventional radio frequency (RF) link that is traditionally used to effect communications between local and remote systems as is known in the art. The communication link between communications device 112 and external system 114 may be implemented using a short-range wireless communication interface, such as an interface conforming to a known communications standard, such as a Bluetooth standard, IEEE 802 standards (e.g., IEEE 802.11), or other public or proprietary wireless protocol.

Figure 9B:
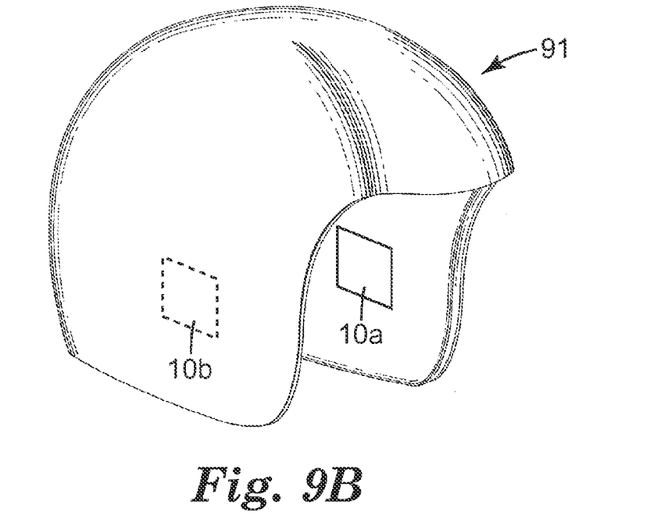
FIG. 9b shows a helmet that incorporates sensors of the present invention.

FIG. 9b shows a helmet 91 that incorporates sensors 10a and 10b of a type described herein. According to the embodiment shown in FIG. 9b, sensors 10a and 10b may be implemented to provide enhanced hearing by the wearer of the helmet 91, and may further provide for ambient noise cancellation such as in the manner described previously with reference to FIG. 2. Sensors 10a and 11b or other sensor may be implemented to serve as a voice pick-up, the performance of which may be enhanced by an ambient noise cancellation capability of a type previously described. Various devices and apparatuses that may be implemented to include one or more sensors of the present invention are disclosed in U.S. Pat. Nos. 4,756,028; 5,515,865; 5,853,005; and D433,776, which are hereby incorporated herein by reference.

Figure 10:
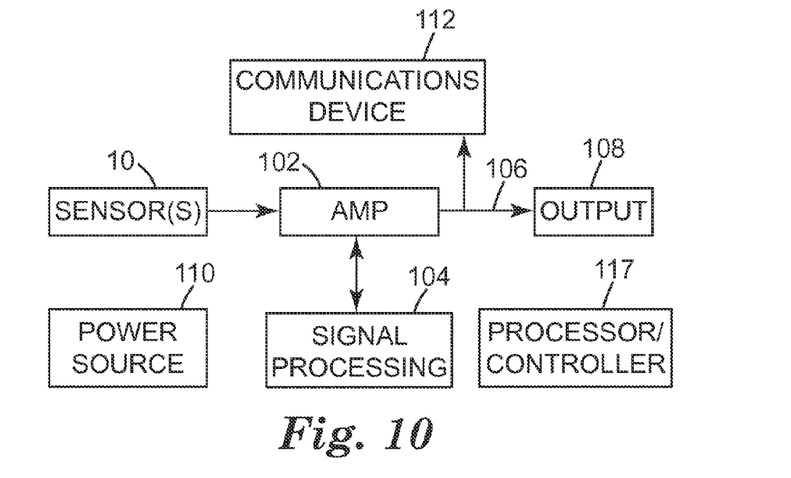
FIG. 10 is a block diagram of circuitry of a sensor in accordance with an embodiment of the present invention.

FIG. 10 is a block diagram showing various components of a sensor 10 in accordance with an embodiment of the present invention. According to the embodiment shown in FIG. 10, one or more sensors 10 of a type described previously is/are coupled to an amplifier 102, typically in accordance with a differential configuration. In an implementation that employs several sensors 10 or multiple transducers, each may be coupled to a separate amplifier 102. The amplifier 102 may include a first stage that is located on the transducer assembly, such as on or near the anchoring end of the transducer. This first amplifier stage, if needed, may serve primarily to convert a high impedance of the transducer, such as a piezoelectric transducer, to a low, less noise susceptible impedance. A second stage amplifier may be used to amplify the sense signal produced at the output of the first stage.

Signal processing circuitry 104 may be coupled to the amplifier 102. The sophistication of the signal processing circuitry 104 may vary from simple to complex. For example, signal processing circuitry 104 may include a simple notch filter having a center frequency of 60 Hz for purposes of attenuating noise due to common power sources. Signal processing circuitry 104 may include one or more bandpass filters that enhance the sensitivity and/or signal-to-noise ratio of transducer signal content of interest.

More sophisticated filtering may be performed on the sense signal to enhance detection of particular body sounds of interest. Such filters may include analog and/or digital filters. Relatively sophisticated analog and digital signal processors may be used to provide for more complex signal processing, such as pattern recognition, source separation, feature correlation, and noise cancellation.

A communications device 112 may be coupled to an output of the amplifier 102. The communications device 112 may be of a type previously described that provides for a communication link between communications device 112 and external system. A power source 110 provides power to the active components of the sensor. A processor/controller 117 may be incorporated to coordinate the various functions of the componentry shown in FIG. 10. Sense signals produced at the output 108 of amplifier 102 are communicated to downstream components via conductor(s) 106, which may be electrical or optical conductors.

The processor/controller 117 may be configured to perform various diagnostic and calibration operations. For example, it may be desirable to equalize the gain response of each transducer of a given sensor. It may also be desirable to perform a frequency response calibration to "tune" or adjust the "tuning" of the frequency response of the transducer(s). The gain and/or frequency response of each transducer may be adjusted during a calibration routine so that each is at a pre-established amplitude and/or exhibits a desired frequency response. Calibration may be initiated before or during use of the sensor, and may be coordinated by the processor/controller 117. In one configuration, an excitation source may be included with the sensor (internal or external) that generates excitation signals having known characteristics, allowing for relatively easy and accurate calibration of transducer gain and/or frequency response.

Figure 11:
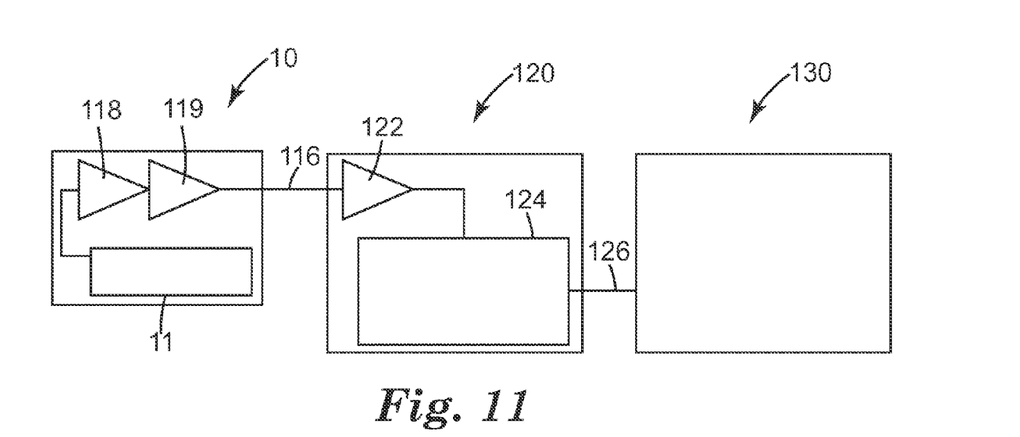
FIG. 11 is a diagram of circuitry for communicating signals produced by a sensor using optical fiber in accordance with an embodiment of the present invention.

According to one embodiment, and as shown in FIG. 11, an impedance conversion amplifier 118 may be implemented at or near to the transducer 11 that is directly interfaced to an analog fiber optic transmitter 119. The output of the fiber optic transmitter 119 is connected to an optical guide 116, which is connected to receiver circuitry 120. Receiver circuitry 120 includes an analog fiber optic receiver 122 that converts the light signal transmitted via the optical guide 116 back to an electrical signal. The output of the optical receiver 122 is coupled to circuitry 124 that may include additional amplification, signal processing and/or a system to record the signal/data communicated over the optical guide 116. Receiver circuitry 120 may be coupled to an additional device or circuitry 130 via electrical or wireless link 126. The additional device or circuitry 130 may be an audio output device, such as earphones, an electronic information device, such as a PDA or PC, a display device, or a network interface.

The housing in FIG. 11 that contains the piezoelectric transducer 14 may contain a small battery to power the impedance conversion amplifier 112 and optical transmitter 114, or two small wires can be included in a bundle with the fiber optic guide or cable 116 for supplying power to these and other active components.

Signal conditioning or processing circuitry can be located at, near or be integrally associated with the transducer 11. For example, the transducer 11 and the signal processing circuitry may be a unitary structure. The signal conditioning or processing circuitry may include one or more of amplification circuitry, such as buffer, gain and/or impedance matching amplification circuitry, filter circuitry, signal conversion circuitry, and more sophisticated circuitry.

Figure 12A:
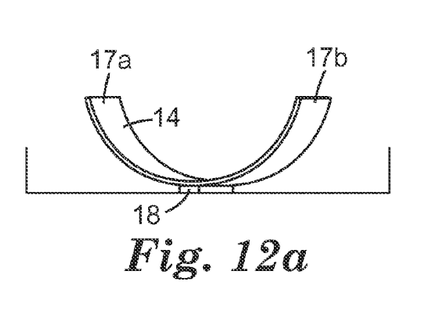
FIGS. 12a-12f illustrate various useful sensor configurations in accordance with embodiments of the present invention.
Figure 12B:
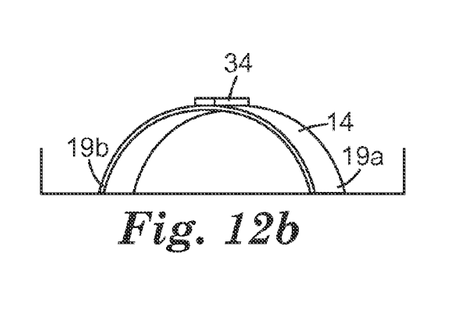

FIGS. 12a-12f illustrate a variety of transducer configurations implemented in accordance with the present invention. FIG. 12a shows a cantilevered bioacoustic transducer 14 having a generally arcuate shape, a single anchoring arrangement 18, and two free ends 17a, 17b. FIG. 12b shows a bioacoustic transducer 14 that is an inverted version of the transducer shown in FIG. 12a. The transducer 14 shown in FIG. 12b has an anchoring arrangement that includes two anchoring ends 19a, 19b. A mass element 34 is positioned on the transducer 14 at a mid-point between the two anchoring ends 19a, 19b.

Figure 12C:
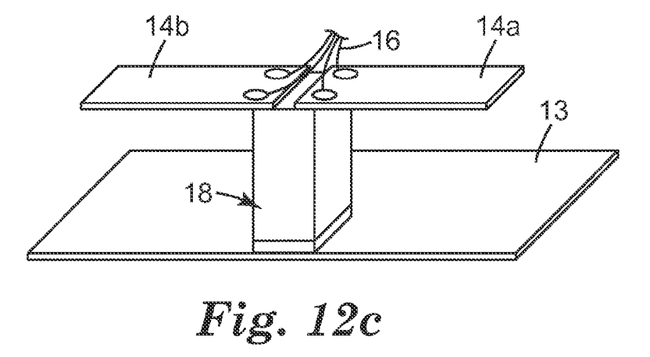
Figure 12D:
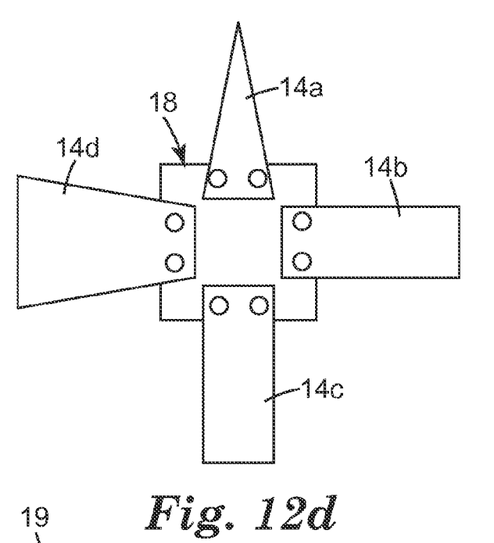

FIG. 12c shows a transducer assembly that includes two independent cantilevered bioacoustic transducers 14a, 14b mounted to a common anchoring arrangement 18. The transducers 14a, 14b are shown as being of the same build, but may be of differing type and/or technology. FIG. 12d shows four cantilevered bioacoustic transducers 14a-14d mounted to a common anchoring arrangement 18. Several of the transducers 14a-14d shown in FIG. 12d differ in terms of shape, and provide for differing frequency response.

Figure 12E:
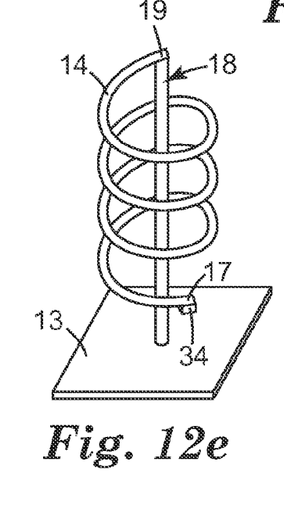
Figure 12F:
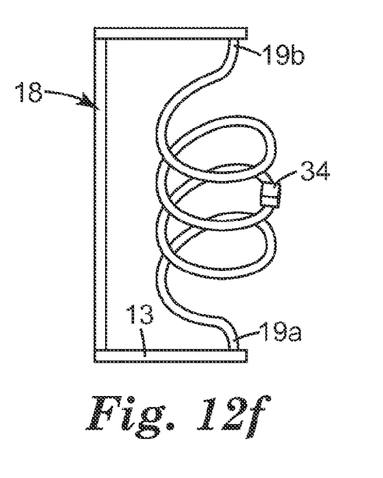

FIG. 12e shows a spring-like cantilevered bioacoustic transducer 14 having an anchoring end 19 connected to a post-like anchoring arrangement 18. A mass element 34 is situated at or near the free end 17 of the transducer 14. FIG. 12f shows a spring-like bioacoustic transducer 14 having two anchoring ends 19a, 19b connected to a post-like anchoring arrangement 18. A mass element 34 is positioned on the transducer 14 at a mid-point between the two anchoring ends 19a, 19b. It is understood that moving the mounting location of mass element 34 along the length of the transducer 14 would change the frequency response and the sensitivity of transducer 14.

Signal conditioning or processing circuitry can be located at, near or be integrally associated with the transducer 11. For example, the transducer 11 and the signal processing circuitry may be a unitary structure. The signal conditioning or processing circuitry may include one or more of amplification circuitry, such as buffer, gain and/or impedance matching amplification circuitry, filter circuitry, signal conversion circuitry, and more sophisticated circuitry.

A bioacoustic sensor of the present invention provides for exceptional sensitivity and signal-to-noise ratio by use of a transducer operable in a cantilever mode. Enhanced sensitivity and signal-to-noise ratio may be realized using transducers of the present invention operable in modes other than a cantilever mode. The performance of a sensor having a cantilevered transducer was verified using a phonocardiogram. Different heart sounds related to different diseases were regenerated in terms of sound, via a compact disk, and phonocardiogram (PCS) using this sensor. There was little difference between the original sound recorded on the CD and the regenerated sensor sounds. The sensor was found to be so sensitive that it can achieve a very good signal-to-noise ratio even when placed over the clothing of the patient.

The foregoing description of the various embodiments of the invention has been presented for the purposes of illustration and description. It is not intended to be exhaustive or to limit the invention to the precise form disclosed. Many modifications and variations are possible in light of the above teaching. For example, sleep disorders by themselves and as indicators of more serious neurological diseases are on the rise. Sleep apnea at all ages and sudden infant death syndrome in babies are also on the rise while their etiology is being identified. A method of diagnosis may involve monitoring body movements and breath/lung sounds of patients with the above indications, which may be readily performed using sensors of the kind described herein. Also, a sensor of the present invention may be used in applications other than bioacoustic sensing applications. It is intended that the scope of the invention be limited not by this detailed description, but rather by the claims appended hereto.

What is claimed is:

1. A sensor for sensing bioacoustic energy, comprising:
a housing comprising an interfacing portion, the interfacing portion of the housing configured to establish coupling with a body part during use of the sensor;
a transducer assembly comprising:
an anchoring arrangement, and
a transducer, the transducer comprising a polymeric piezoelectric film adapted to modulate or generate an electrical signal in response to deformation, the transducer including only one free end and being cantilevered, the transducer being fixedly coupled to the housing at an anchoring location via the anchoring arrangement such that the transducer is arranged to be preferentially sensitive to bioacoustic energy transferred to the transducer via the interfacing portion of the housing relative to other portions of the housing; and
at least one conductor coupled to the transducer.

2. The sensor of claim 1, wherein the anchoring arrangement comprises a compliant or a rigid coupling arrangement configured to couple the transducer to the housing.

3. The sensor of claim 1, wherein the anchoring arrangement defines a unitary structure of the housing.

4. The sensor of claim 1, comprising a fixing arrangement coupled to the housing and configured to establish affixation between the housing and the body part during use, the fixing arrangement comprising one or both of an adhesive and elastic bands.

5. The sensor of claim 1, wherein the at least one conductor comprises at least one optical conductor.

6. The sensor of claim 1, wherein the housing comprises a base and a cover, the base comprising the interfacing portion and the cover coupled to the base via a compliant joint arrangement.

7. The sensor of claim 1, wherein the interfacing portion of the housing is substantially stiff.

8. The sensor of claim 7, wherein the interfacing portion of the housing comprises a polymeric material, metal or alloy, a composite material, a ceramic material or crystalline material.

9. The sensor of claim 1, wherein the transducer comprises first and second opposing major surfaces, and the first and second major surfaces of the transducer are substantially parallel to the interfacing portion of the housing.

10. The sensor of claim 1, wherein the sensor comprises an arrangement configured to modify a frequency response of the transducer.

11. The sensor of claim 1, further comprising a mass element disposed proximate to the free end of the transducer.

12. The sensor of claim 1, further comprising:
a mass element comprising magnetizable material disposed proximate to the free end of the transducer; and
a magnet arrangement configured to magnetically interact with the magnetizable material of the mass element, the magnet arrangement configured to facilitate adjustment of the interaction between the magnet and the magnetizable material of the mass element.

13. The sensor of claim 1, wherein the transducer is one of a plurality of transducers, and wherein each of the plurality of transducers is configured to have a frequency response differing from that of at least one other transducer of the plurality of transducers.

14. The sensor of claim 1, further comprising:
an auxiliary transducer disposed within the housing other than at the interfacing portion of the housing; and noise cancellation circuitry coupled to the transducer and the auxiliary transducer.

15. A stethoscope comprising the sensor according to claim 1.

16. A helmet comprising one or more sensors according to claim 1.

17. The sensor of claim 1, comprising communications circuitry configured to facilitate wired or wireless communication between the sensor and a device external of the housing.

18. The sensor of claim 1, wherein the transducer comprises a single anchoring end coupled to the anchoring arrangement.

19. The sensor of claim 1, wherein the anchoring arrangement comprises a pedestal having a first end and a second end, the first end of the pedestal coupled to the interfacing portion of the housing and the second end of the pedestal coupled to the transducer.

20. The sensor of claim 1, further comprising a mass element disposed on the transducer.

* * * * *

UNITED STATES PATENT AND TRADEMARK OFFICE
CERTIFICATE OF CORRECTION

PATENT NO. : 8,024,974 B2
APPLICATION NO. : 11/286883
DATED : September 27, 2011
INVENTOR(S) : Vivek Bharti It is certified that error appears in the above-identified patent and that said Letters Patent is hereby corrected as shown below:

<u>Title Page 2, Column 2 (Other Publications)</u>
Line 5                    Delete "Analusis," and insert -- Analysis, --, therefor.

<u>Column 7</u>
Line 46                   Delete "SBS," and insert -- $S_{BS}$, --, therefor.

<u>Column 10</u>
Line 27                   Delete "14a-14nmay" and insert -- 14a-14n may --, therefor.

<u>Column 11</u>
Line 18                   Delete "loose" and insert -- lose --, therefor.

<u>Column 13</u>
Line 34                   Delete " 11b" and insert -- 10b --, therefor.

<u>Column 15</u>
Line 12 (Approx.)         Delete "14a-14dmounted" and insert -- 14a-14d mounted --, therefor.

Signed and Sealed this
Fifteenth Day of May, 2012

David J. Kappos
*Director of the United States Patent and Trademark Office*